(12) United States Patent
Belbachir et al.

(10) Patent No.: US 8,529,968 B2
(45) Date of Patent: Sep. 10, 2013

(54) DECONTAMINATING COMPOSITION HAVING SIMULTANEOUSLY BACTERICIDAL, FUNGICIDAL AND VIROCIDAL PROPERTIES, METHODS FOR OBTAINING AND USING SAID COMPOSITION

(75) Inventors: Hakima Belbachir, Grenoble (FR); Jean Angelidis, Saint Ismier (FR)

(73) Assignee: Hightech Bio-Activities Holding GmbH, Zurich (CH)

( * ) Notice: Subject to any disclaimer, the term of this patent is extended or adjusted under 35 U.S.C. 154(b) by 1573 days.

(21) Appl. No.: 10/594,782

(22) PCT Filed: Mar. 29, 2005

(86) PCT No.: PCT/FR2005/000747
§ 371 (c)(1),
(2), (4) Date: Jul. 11, 2007

(87) PCT Pub. No.: WO2005/092094
PCT Pub. Date: Oct. 6, 2005

(65) Prior Publication Data
US 2008/0038373 A1   Feb. 14, 2008

(30) Foreign Application Priority Data
Mar. 29, 2004   (FR) ..................................... 04 03207

(51) Int. Cl.
*A61K 36/00*     (2006.01)
*A61K 36/53*     (2006.01)
*A61K 36/54*     (2006.01)
*A61K 36/61*     (2006.01)
*A61K 36/752*    (2006.01)
*A61K 36/8945*   (2006.01)
*A61K 31/19*     (2006.01)

(52) U.S. Cl.
USPC ........... 424/745; 424/725; 424/736; 424/739; 424/742; 424/754; 424/778; 514/568

(58) Field of Classification Search
USPC ................ 424/664, 725, 739, 742, 745, 736, 424/754, 778; 514/568
See application file for complete search history.

(56) References Cited

U.S. PATENT DOCUMENTS

| 5,472,684 A | * | 12/1995 | Nabi et al. | 424/49 |
| 5,733,530 A | * | 3/1998 | Bacca et al. | 424/52 |
| 6,514,551 B1 | | 2/2003 | Schur | |
| 2003/0039578 A1 | | 2/2003 | Belbachir et al. | |
| 2004/0009245 A1 | * | 1/2004 | Vail et al. | 424/742 |

FOREIGN PATENT DOCUMENTS

| EP | 1 116 446 A2 | 7/2001 |
| FR | 2 618 670 | 2/1989 |
| WO | WO-02/09777 | 2/2002 |
| WO | WO-2004/066734 | 8/2004 |

OTHER PUBLICATIONS

Meeker, H., The Antibacterial Action of Eugenol, Thyme Oil, and Related Oils Used in Denistry, 1988, Compendium (Newton, PA), vol. 9, Issue 1, pp. 32, 34-35, 38, and 40-41.*
Thakare, M., Pharmacological Screening of Some Medicinal Plants As Antimicrobial and Feed Additives, Master's Thesis, [online]. VA Polytechnic Institute and State University, 2004 [retrieved on Sep. 24, 2010]. Retrieved from the Internet: <URL:http://scholar.lib.vt.edu/theses/available/etd-08032004-160558/unrestricted/mohanthesis.pdf, pp. 1 ,14-15.*
Aug. 17, 2000, Inhibition of Oxidation of Human Low-Density Lipoproteins by Phenolic Substances in Different Essential Oils Varieties P.L. Teissedre et al. J. Agric. Food Chem 2000 , vol. 48, pp. 3801-3805.

* cited by examiner

*Primary Examiner* — Sue Liu
*Assistant Examiner* — Andriae M Holt
(74) *Attorney, Agent, or Firm* — Jordan and Hamburg LLP

(57) ABSTRACT

The invention concerns a decontaminating composition having simultaneously bactericidal, fungicidal and virocidal properties, comprising as active components eugenol, eugenol acetate, vanillin and carvacrol, characterized in that said active constituents are present in the following percentages by weight: at least about 12% eugenol, at least about 3% eugenol acetate, at least about 0.1% vanillin and at least about 0.5% carvacrol. Said decontaminating composition can be used as liquid or solid soaps. It can also impregnate in liquid form fabrics and nonwoven fabrics such as garments for medical use, bed sheets, slip covers, surgery drape, dressings and gauze such as those applied to the skin of serious burn victims.

6 Claims, No Drawings

DECONTAMINATING COMPOSITION HAVING SIMULTANEOUSLY BACTERICIDAL, FUNGICIDAL AND VIROCIDAL PROPERTIES, METHODS FOR OBTAINING AND USING SAID COMPOSITION

TECHNICAL FIELD OF THE INVENTION

The present invention relates to a decontaminating composition. More particularly, the invention relates to a composition exhibiting at the same time bactericidal, fungicidal and virucidal properties and also to processes for obtaining and to uses of such a composition.

STATE OF THE ART

WO-A-0209777 describes a method for bactericidal, fungicidal, virucidal and insecticidal treatment of ambient air consisting in circulating air through a permeable container in which is placed a treating agent having bactericidal, fungicidal, virucidal and insecticidal effects. The treating agent is made up of crystals of mineral salt, in particular of sodium chloride. The treating agent can also comprise elements of plant origin such as clove. That document also describes a device for implementing the targeted method, comprising, between two mechanical air filtering sheets, a layer of bactericidal, fungicidal and virucidal treating agent distributed uniformly so as to prevent the development of microorganisms on the walls. According to an embodiment, the device comprises in particular a stratum of mineral salts for bactericidal, fungicidal and/or virucidal treatment of the air and a stratum of fragmented plants such as thyme and/or clove.

The device described in WO-A-0209777, and also the bactericidal, fungicidal and virucidal treating agent which is included therein, are specific to the treatment of ambient air.

AIMS OF THE INVENTION

An object of the present invention is to provide a decontaminating composition having at the same time bactericidal, fungicidal and virucidal properties and capable of being adapted to any type of support to be decontaminated.

Another object of the present invention is to provide an effective decontaminating composition having a very broad spectrum of action against pathogens.

Another object of the present invention is also to provide a decontaminating composition which has very good antimicrobial properties with a limited toxicity.

An object of the invention is also to provide a decontaminating composition which can be obtained from nontoxic biological materials.

An object of the invention is also to provide a biodegradable decontaminating composition.

Another object of the present invention is also to provide a decontaminating composition which can be readily obtained from relatively inexpensive components.

Another object of the invention is also to provide a decontaminating composition which can be ingested by humans and animals.

An object of the invention is also to make it possible to limit the proliferation of green algae often encountered in decontamination treatments.

Other objects and advantages of the invention will emerge on reading the description hereinafter.

SUMMARY OF THE INVENTION

These objects, and others, are satisfied by the present invention, which provides a decontaminating composition exhibiting at the same time bactericidal, fungicidal and virucidal properties, comprising, as active components, eugenol, eugenol acetate, vanillin and carvacrol, characterized in that said active components are present in a proportion of at least approximately 12% by weight for eugenol, at least approximately 3% by weight for eugenol acetate, at least approximately 0.1% by weight for vanillin and at least approximately 0.5% by weight for carvacrol.

The simultaneous presence of the four active components: eugenol, eugenol acetate, vanillin and carvacrol, in the stated amounts, is essential. The compulsory presence of at least approximately 0.1% by weight of vanillin is particularly important.

DETAILED DESCRIPTION OF PREFERRED EMBODIMENTS

According to a preferred embodiment of the invention, the four active components of the decontaminating composition: eugenol, eugenol acetate, vanillin and carvacrol are contained in plant elements.

The eugenol and the eugenol acetate of the decontaminating composition are advantageously contained in clove.

The vanillin of the decontaminating composition is preferably contained in vanilla.

The carvacrol of the decontaminating composition is, for example, contained in oregano.

The carvacrol of the decontaminating composition can also be contained in savory.

Although not preferred, the decontaminating compositions in which at least one of the active components is not contained in a plant element are, however, within the context of the invention.

It should be noted that, for some applications, problems of toxicity may be encountered if the proportions of eugenol and/or of eugenol acetate and/or of carvacrol are too great. In each case, those skilled in the art will readily determine, by means of routine tests, the proportions of eugenol, of eugenol acetate and of carvacrol which should not be exceeded.

According to another characteristic of the invention, the decontaminating composition also comprises thymol as active component.

The thymol is advantageously contained in thyme.

When thymol is present, the decontaminating composition of the invention preferably comprises at least approximately 0.5% by weight thereof.

According to one embodiment of the invention, the decontaminating composition also comprises at least one mineral salt as active component.

This mineral salt is, for example, chosen from chlorides, carbonates, silicates and sulphates of alkali metals, of ammonium, of alkaline earth metals, of aluminium or of magnesium, and alums.

According to one arrangement of the invention, the mineral salt is chosen from sodium chloride and sodium bicarbonate.

The sodium chloride is preferably contained in grey salt, i.e. when it is present, the sodium chloride is advantageously added in the form of grey salt.

The mineral salt, when it is present, represents in general at least approximately 0.5% by weight of the decontaminating composition.

A particularly preferred decontaminating composition according to the present invention comprises, as active components, eugenol, eugenol acetate, vanillin, carvacrol and thymol, with the following percentages by weight:

eugenol: 15-25
eugenol acetate: 3-5 vanillin: 0.25-0.35
carvacrol: 0.7-1.2
thymol: 0.7-1.2

The composition also comprises inert material, the nature of which depends on the form in which the composition is used and on the intended use.

According to an advantageous arrangement of the invention, the eugenol, the eugenol acetate, the vanillin, the carvacrol and the thymol of this preferred decontaminating composition are contained in plant elements.

The decontaminating composition of the invention can also comprise at least one trace element, for example copper, gold, silver, magnesium.

It can also comprise at least one monoterpene, advantageously a monoterpene derived from a plant chosen, for example, from the group consisting of pine and fir.

The decontaminating composition of the invention may also contain at least one monoterpene alcohol, advantageously a monoterpene alcohol derived from a plant chosen, for example, from the group consisting of rosewood, peppermint and lemon grass.

The decontaminating composition of the invention can also contain at least one aromatic aldehyde such as an aromatic aldehyde derived, advantageously, from a plant chosen, for example, from the group consisting of cinnamon, cumin, lavender, etc.

It can also contain at least one sulphur-containing compound derived, advantageously, from a plant chosen, for example, from the group consisting of garlic and onion.

It can also comprise at least one nitrogenous compound derived, advantageously, from a plant element, for example, from *citrus reticulata* or *citrus paradisi*.

It is particularly advantageous for the phenols and the aldehydes present in the decontaminating composition of the invention to be of plant origin.

It is also desirable to take phenols from several extracts of different plants.

In an advantageous embodiment of the invention, the decontaminating composition of the invention contains extracts of plants below:

*eugenia caryophylatta*
at least one *origanum* chosen from *origanum heracleoticum* and *origanum majorana*
*vanilla planifolia* Andrews.

Better still, for the latter embodiment, the decontaminating composition contains, in addition to the above plant extracts, one or more extracts of plants chosen from the following:

*artemisia dracunculus* L.
*carum carvi*
*chamaemelum nobile*
*cinnamomum zeylanicum*
*cinnamomum camphora*
*citrus paradisi*
*coriandrum sativum*
*cuminum cyminum*
*eucalyptus radiata*
*hyssopus officinalis*
*juniperus communis*
*lavandula officinalis*
*lippia citriodora*
*melissa officinalis*
*mentha piperita*
*myristica fragrans*
*ocimum gratissimum*
*urtica dioica*
*pimpinella anisum*
*pinus pinaster*
*rosmarinus officinalis*
*salvia officinalis*
*satureja montana*
*sesamum indicum*
*thymus vulgaris*
*zingiber officinalis* and also elements chosen from sodium bicarbonate, sodium chloride and hydrophilic colloids such as clays.

The amounts of the various extracts and elements present in the decontaminating composition will be adjusted by those skilled in the art so that the percentages by weight of eugenol, of eugenol acetate, of vanillin and of carvacrol of the decontaminating composition are those specified above, i.e. at least approximately 12% by weight for eugenol, at least approximately 3% by weight for eugenol acetate, at least approximately 0.1% by weight for vanillin and at least approximately 0.5% by weight for carvacrol.

A particularly preferred decontaminating composition is given hereinafter:

| | |
|---|---|
| clay/hydrophilic colloids = | 12.0 % by weight |
| *artemisia dracunculus* = | 0.5 % by weight |
| sodium bicarbonate = | 1.0 % by weight |
| *carum carvi* = | 1.5 % by weight |
| *chamaemelum nobile* = | 0.5 % by weight |
| *cinnamomum zeylanicum* = | 0.5 % by weight |
| *cinnamomum camphora* = | 0.1 % by weight |
| *citrus paradisi* = | 0.1 % by weight |
| *coriandrum sativum* = | 1.0 % by weight |
| *cuminum cyminum* = | 2.0 % by weight |
| *eucalyptus radiata* = | 5.0 % by weight |
| *eugenia caryophylatta* = | 23.1 % by weight |
| *hyssopus officinalis* = | 1.0 % by weight |
| *juniperus communis* = | 0.5 % by weight |
| *lavandula officinalis* = | 5.0 % by weight |
| *lippia citriodora* = | 0.5 % by weight |
| *melissa officinalis* = | 0.5 % by weight |
| *mentha piperita* = | 0.5 % by weight |
| *myristica fragrans* = | 0.5 % by weight |
| *ocimum gratissimum* = | 0.5 % by weight |
| *origanum heracleoticum* = | 5.0 % by weight |
| *origanum majorana* = | 5.0 % by weight |
| *urtica dioica* = | 5.0 % by weight |
| *pimpinella anisum* = | 0.5 % by weight |
| *pinus pinaster* = | 2.0 % by weight |
| *rosmarinus officinalis* = | 10.0 % by weight |
| *salvia officinalis* = | 1.0 % by weight |
| *satureja montana* = | 1.0 % by weight |
| *sesamum indicum* = | 5.0 % by weight |
| *thymus vulgaris* = | 5.0 % by weight |
| *vanilla planifolia* Andrews = | 1.2 % by weight |
| *zingiber officinalis* = | 2.0 % by weight |
| sodium chloride = | 1.0 % by weight. |

When the active components of the decontaminating composition of the invention are synthetic elements,—not preferred—said composition can be prepared by simple mixing of said components at ambient temperature.

The invention also provides a method for producing the decontaminating composition described, when the four active components: eugenol, eugenol acetate, vanillin and carvacrol, are contained in plant elements,—preferred—for example the eugenol and the eugenol acetate in clove, the vanillin in vanilla and the carvacrol in oregano or in savory.

The method for producing a decontaminating composition of the invention in which the four active components are contained in plant elements is characterized in that it comprises:

(a) a first step consisting in grinding said pre-dried plant elements, said grinding step producing a powder having a mean particle size ranging from approximately 0.5 mm to approximately 1.2 mm, (b) a second step consisting in macerating said powder, at ambient temperature, in a solution for at least 12 hours, preferably for approximately 24 hours, resulting in a maceration solution or juice and residual inert plant material.

In step (a) above, the particle size will be adjusted by those skilled in the art according to the diffusibility of the active ingredients targeted.

The decontaminating compositions containing, in plant form, additional active components in relation to the four "basic active components" (eugenol, eugenol acetate, vanillin and carvacrol) can be prepared in the same manner as that described above.

For certain forms of the decontaminating composition, such as, for example, the production of a biodecontaminating liquid, maceration under cold conditions is appropriate so as not to destroy or weaken the active elements. A maceration of typically 72 hours is effective.

The maceration step at ambient temperature is carried out in an aqueous, oily or alcoholic solution.

If the solution is an aqueous solution, it is used to isolate the water-soluble elements.

The maceration solution is then usually separated from the residual inert plant material.

The maceration solution can be used to form a solid product, by impregnating, by deposition or absorption, a plant or mineral support.

Consequently, after the second step, referred to as maceration step, the method can comprise a third step consisting in impregnating, by deposition or absorption, the maceration solution onto a support chosen from inert, usually porous, plant supports and mineral supports.

The mineral support is, for example, chosen from the group consisting of talc, of active charcoal and of mineral salts, such as, for example, sodium chloride and sodium bicarbonate.

The support may also be chosen from hydrophilic colloids such as clays.

The support can also consist of dried inert plant material, for example the residual inert plant material, but another inert plant material can also be used.

The resulting product can then be dried, for example in a dehumidifying oven, or else stored in wet form, according to the applications.

The inert residual plant material used as support according to the invention will usually be dried.

For certain applications, in particular for pressure cleaning of floors, the residual inert plant material will advantageously be left as it is, without drying, and the decontaminating composition will be in the form of a liquid suspension.

The choice of the form and of the nature of the inert support is made according to the application envisaged. For example, the inert support will advantageously be in the form of large-diameter beads for filtrations, in the form of cloth in order to obtain a biodecontaminating cloth, etc.

When the decontaminating composition comprises thymol contained in thyme, this can be added, once it has been dried, during the first grinding step, at the same time as the plant elements containing the eugenol, the eugenol acetate, the vanillin and the carvacrol.

In the clove, it is advantageous to use only the head, but it is possible to use the whole flower.

When the decontaminating composition comprises a mineral salt, this is ground, to a particle size of approximately 0.1 to 0.5 mm, and it is then added to the solution containing the ground plant elements before, during or after the maceration.

When the decontaminating composition comprises one or more trace elements, these can be added to the maceration solution.

It is also possible, although it is not the preferred embodiment, to prepare a decontaminating composition according to the invention, in which the active components are contained in plant elements, by grinding, intimate mechanical mixing and sieving of said pre-dried plant elements, without carrying out the maceration step. A decontaminating composition obtained according to this latter procedure remains effective but generally less so than that prepared according to the preferred method using a maceration step; it is also less homogeneous and it may thus be more difficult to ensure constant characteristics.

The decontaminating composition of the invention in liquid form is produced from the decontaminating composition in solid form, for example by:

soaking said decontaminating composition in solid form in water, which may or may not be sterile according to the applications, another liquid such as an alcohol or an oil, etc., passing warm or hot water, which may or may not be sterile according to the applications, through the decontaminating composition in solid form, for example in grains, passing other liquids through the decontaminating composition in solid form.

In the latter two methods, the liquid collected after passage through the decontaminating composition in solid form constitutes the decontaminating composition in liquid form.

The decontaminating composition of the present invention simultaneously exhibits bactericidal, fungicidal and virucidal properties which can make it possible to decontaminate a very large number of media and supports.

The decontaminating composition of the invention can, for example, be used in the form of liquid or solid soaps, or of powder sachets intended to be placed in household appliances such as in the bag of a vacuum cleaner, or in the compartment intended for the cleaning product of a dishwasher or of a washing machine. It can also be placed in domestic animal litter in order to disinfect it and to reduce odours therefrom. It can also be contained in paints, in particular water-based paints, adhesives, tapestries, wallpapers, floorings, insoles, chipboard, etc. It can also impregnate, in liquid form, fabrics or non-wovens such as clothing for medical use, sheets, covers, operative fields, dressings, gauzes which can be used, for example, for application to the skin of victims of third-degree burns, towelettes, etc. The fabrics and the non-wovens treated with the decontaminating composition according to the invention are not only sterile but also biodecontaminant.

In a particularly advantageous embodiment of the present invention, the decontaminating composition is integrated, in the production process, into a material, resulting in a biodecontaminant material. The material is, for example, a plastic material, a paper, a non-woven. It is thus possible to obtain, for example, biodecontaminant toys, keys on a keyboard, lift buttons. The decontaminating composition of the invention can also be integrated into the process for producing swimming pool floors.

Several methods of integrating the decontaminating composition of the invention exist for the production of biodecontaminating materials:

Method by granular deposit maintained mechanically in a filter, with a prefilter which acts as a mechanical retainer of the granular decontaminating composition (this prefilter can also be treated with the decontaminating composition).

Method of integration into a fibrous medium. This method of integrating a decontaminating composition in granular form into a filtering medium allows the biodecontaminating particles to be retained by the very fibres of the substrate.

Method of integration into the filtering medium at the moment it is produced: the decontaminating composition in granular form is deposited onto the fibres (for example, glass fibres) at the moment the medium is produced, while the latter is not yet dry. Removal of liquids and drying are subsequently carried out.

Method by integration into the binder in liquid form at the moment the filtering medium is produced. The decontaminating composition in liquid form is mixed with the binder. Removal of liquids and drying are subsequently carried out.

Method by deposition of a decontaminating composition in liquid form by soaking: the filtering medium (fibre, fabric, paper) is passed through the decontaminating composition in liquid form and is subsequently dried. The support thus treated becomes biodecontaminating. It can be used to produce filtering media (masks, filters, etc.), and biodecontaminating clothing which can be used in hospital environments, but also by firefighters or for domestic use.

The decontaminating composition of the invention can also be mixed in granular form in soaps. The decontaminating composition in grains is mixed with soap paste which is subsequently sent on to the usual moulding process for producing soap.

The decontaminating composition of the invention can also be mixed into liquid soaps and other household products or toiletries. The mixing is carried out between two liquids at ambient temperature for the amount of time necessary to obtain a paste or a liquid which has a uniform colour demonstrating the homogeneity of the mixture.

The treatment of water or of liquids is carried out either by passage through a filter containing the decontaminating composition of the invention in a solid form with a given particle size according to the application, or directly with the decontaminating composition in the form of a liquid mixed with the liquid to be treated.

When its active components are contained in plants, the decontaminating composition of the invention can also, for certain concentrations of the active elements, be ingested, in particular as a food supplement, for example in the form of a powder, of cachets or of tablets.

The invention will now be described in greater detail with reference to the non-limiting examples hereinafter.

Example 1

A decontaminating composition containing:

| | |
|---|---|
| eugenol | 20% by weight |
| eugenol acetate | 4.0% by weight |
| vanillin | 0.3% by weight |
| carvacrol | 1.0% by weight |
| thymol | 1.0% by weight |
| inert plant material | qs 100 | was prepared as follows.

Cloves were dried at low temperature, i.e. at approximately 30° C.

The heads of the dried cloves were separated.

Oregano, thyme (flowers and leaves) and vanilla were dried at approximately 30° C.

The dried plants, namely 80 g of clove heads, 15 g of thyme (flowers and leaves), 1.5 g of vanilla and 3.5 g of savory, were mixed.

The dried plant mixture was ground and sieved until a mean particle size of 0.5 mm was obtained.

The ground and sieved mixture was macerated at ambient temperature for 24 hours in solution in 100 ml of deionized water.

Maceration juice and inert residual plant material were thus obtained.

The maceration juice was extracted and the pre-dried inert residual plant material was impregnated therewith.

The impregnated inert residual plant material was dried in a dehumidifying oven so as to obtain 100 g of composition in the form of a brown powder with a mean particle size of 0.5 mm.

In solution in 10 ml of distilled deionized water, its pH is approximately 4.

A suspension of the bacterium *Mycobacterium tuberculosis* was prepared, incorporating, under a vertical laminar flow hood, $10^5$ CFU/ml (CFU signifies the number of colony-forming units per ml) into an agar.

The suspension was then poured into three Petri dishes, where it solidified.

0.1 g, 0.25 g and 0.5 g, respectively, of the decontaminating composition prepared above were added to each of the three Petri dishes.

After incubation for four weeks at 37° C., the three Petri dishes exhibited a halo of inhibition around the cupules containing the decontaminating powder, which demonstrates the antibactericidal activity of the decontaminating composition tested for the three amounts indicated, even with an amount as low as 0.1 g.

Example 2

Three millilitres of a suspension containing approximately $10^6$ CFU/ml of the bacterium *Pseudomonas aeroginosa* were deposited, with three millilitres of nutrient broth, in five test tubes.

0.1 g, 0.25 g, 0.5 g, 0.75 g and 1 g, respectively, of the decontaminating composition of Example 1 were added to each of the five test tubes.

The five test tubes were incubated for 24 hours at 37° C.

It was noted that the minimum inhibitory concentration for the decontaminating composition tested was 0.25 g per 6 ml.

Example 3

Three millilitres of a suspension containing approximately $10^6$ CFU/ml of the bacterium *Staphylococcus aureus* were deposited, with three millilitres of nutrient broth, in five test tubes.

0.1 g, 0.25 g, 0.5 g, 0.75 g and 1 g, respectively, of the decontaminating composition of Example 1 were added to each of the five test tubes.

The five test tubes were incubated for 24 hours at 37° C.

It was noted that the minimum inhibitory concentration for the decontaminating composition tested was 0.1 g per 6 ml.

Example 4

Three millilitres of a suspension containing approximately $10^6$ CFU/ml of the fungus *Candida albicans* were deposited, with three millilitres of nutrient broth, in five test tubes.

0.1 g, 0.25 g, 0.5 g, 0.75 g and 1 g, respectively, of the decontaminating composition of Example 1 were added to each of the five test tubes.

The five test tubes were incubated for 24 hours at 30° C.

It was noted that the minimum inhibitory concentration for the decontaminating composition tested was 0.1 g per 6 ml.

Example 5

Three millilitres of a suspension containing approximately $10^6$ CFU/ml of the fungus *Aspergillus niger* were deposited, with three millilitres of nutrient broth, in five test tubes.

0.1 g, 0.25 g, 0.5 g, 0.75 g and 1 g, respectively, of the decontaminating composition of Example 1 were added to each of the five test tubes.

The five test tubes were incubated for 24 hours at 30° C.

It was noted that the minimum inhibitory concentration for the decontaminating composition tested was 0.75 g per 6 ml.

Example 6

Three millilitres of a suspension containing approximately $10^6$ CFU/ml of the bacterium *Legionella pneumophila* were deposited, with three millilitres of nutrient broth, in five test tubes.

0.1 g, 0.25 g, 0.5 g, 0.75 g and 1 g, respectively, of the decontaminating composition of Example 1 were added to each of the five test tubes.

The five test tubes were incubated for 24 hours at 37° C.

It was noted that the minimum inhibitory concentration for the decontaminating composition tested was 0.1 g per 6 ml, i.e. a product diluted to 1.7%.

Example 7

The aim of this example is to determine the evolution of the bacterium *Pseudomonas aeroginosa* as a function of exposure time with the decontaminating composition of Example 1.

The bacterium *Pseudomonas aeroginosa* is a bacterium which is present in soil and in water and which is capable of infecting the human body via the respiratory pathways.

The bacterial strain was reconstituted in a nutritive bath, it was incubated at 35° C. for 24 hours and was centrifuged at 2500 rpm for 10 minutes.

The supernatant was removed and the remaining microbial pellet was then washed three times with sterile buffered deionized water.

The pellet was then resuspended in 50 ml of sterile buffered deionized water.

100 ml of sterile buffered deionized water containing $1 \times 10^6$ CFU/ml of the bacterium *Pseudomonas aeroginosa* and, respectively, 0 g, 1 g, 5 g, 10 g and 25 g of the decontaminating composition of Example 1 were added to five 250 ml Erlenmeyer flasks.

The five flasks were placed in a vibrating rotary device at 50 rpm at 25° C.

1 ml was removed from each flask after 0 hour, 4 hours and 24 hours, and was transferred into 1 ml of a neutralizing solution.

Table I below indicates the CFU/ml concentration of the bacterium *Pseudomonas aeroginosa* contained in the samples taken.

TABLE I

| Exposure time h | 0 g | 1 g | 5 g | 10 g | 25 g |
| --- | --- | --- | --- | --- | --- |
| 0 | $3.4 \times 10^6$ | $2.8 \times 10^6$ | $3.7 \times 10^6$ | $62.9 \times 10^6$ | $64.4 \times 10^6$ |
| 4 | $4.0 \times 10^6$ | $<1.0 \times 10^1$ | $<1.0 \times 10^1$ | $<1.0 \times 10^1$ | $<1.0 \times 10^1$ |
| 24 | $7.2 \times 10^7$ | $<1.0 \times 10^1$ | $<1.0 \times 10^1$ | $<1.0 \times 10^1$ | $<1.0 \times 10^1$ |

As indicated in Table I, after 4 hours, it can be considered that the decontaminating composition has eliminated the bacterium Pseudomonas aeroginosa since it has caused its concentration to drop substantially by a factor of $10^5$.

Example 8

Example 7 was repeated with the bacterium *Staphylococcus aureus*.

Table II below indicates the CFU/ml concentration of the bacterium *Staphylococcus aureus* contained in the samples taken.

TABLE II

| Exposure time h | 0 g | 1 g | 5 g | 10 g | 25 g |
| --- | --- | --- | --- | --- | --- |
| 0 | $4.2 \times 10^6$ | $2.9 \times 10^6$ | $4.0 \times 10^6$ | $4.1 \times 10^6$ | $3.7 \times 10^6$ |
| 4 | $4.7 \times 10^6$ | $<1.0 \times 10^1$ | $<1.0 \times 10^1$ | $<1.0 \times 10^1$ | $4.0 \times 10^1$ |
| 24 | $3.9 \times 10^7$ | $<1.0 \times 10^1$ | $<1.0 \times 10^1$ | $<1.0 \times 10^1$ | $2.3 \times 10^1$ |

As indicated in Table II, after 4 hours, the decontaminating composition has eliminated most of the bacterium *Staphylococcus aureus* and has caused the concentration to drop substantially by a factor of $10^5$.

Example 9

The *Staphylococcus aureus* bacterial strain was reconstituted in a nutritive bath, it was incubated at 35° C. for 24 hours and was centrifuged at 2400 rpm for 10 minutes.

The supernatant was removed and the remaining microbial pellet was then washed three times with sterile buffered deionized water.

The pellet was then resuspended in 50 ml of sterile buffered deionized water.

100 ml of sterile buffered deionized water containing $1 \times 10^6$ CFU of the bacterium *Staphylococcus aureus* and 25 g of the decontaminating composition of Example 1 were added to a 250 ml Erlenmeyer flask.

The flask was placed in a vibrating rotary device at 50 rpm at 25° C.

1 ml was removed from the flask after 1 minute and was transferred into 1 ml of a neutralizing solution.

It was noted that the bacterium *Staphylococcus aureus* had been completely eliminated.

Example 10

The decontaminating composition of Example 1 was tested against human *Coronavirus* type ATTC VR-740, strain $229^E$, similar to the coronavirus responsible for SARS or severe acute respiratory syndrome. It was noted that the decontaminating composition, in a proportion of 1:10 in a buffered suspension, deactivates 99.97%, i.e. at least 3.6 $\log_{10}$ of the virus, in 10 minutes.

Those skilled in the art will understand that, although the invention has been described and illustrated for particular embodiments, many variants can be envisaged while at the same time remaining within the context of the invention as defined in the attached claims.

The invention claimed is:

1. A Decontaminating composition exhibiting at the same time bactericidal, fungicidal and virucidal properties, comprising, as active components, eugenol, eugenol acetate, vanillin and carvacrol, the composition comprising ingredients, in the following amounts:

| | |
|---|---|
| clay/hydrophilic colloids = | 12.0 % by weight |
| *artemisia dracunculus* = | 0.5 % by weight |
| sodium bicarbonate = | 1.0 % by weight |
| *carum carvi* = | 1.5 % by weight |
| *chamaemelum nobile* = | 0.5 % by weight |
| *cinnamomum zeylanicum* = | 0.5 % by weight |
| *cinnamomum camphora* = | 0.1 % by weight |
| *citrus paradisi* = | 0.1 % by weight |
| *coriandrum sativum* = | 1.0 % by weight |
| *cuminum cyminum* = | 2.0 % by weight |
| *eucalyptus radiata* = | 5.0 % by weight |
| *eugenia caryophylatta* = | 23.1 % by weight |
| *hyssopus officinalis* = | 1.0 % by weight |
| *juniperus communis* = | 0.5 % by weight |
| *lavandula officinalis* = | 5.0 % by weight |
| *lippia citriodora* = | 0.5 % by weight |
| *melissa officinalis* = | 0.5 % by weight |
| *mentha piperita* = | 0.5 % by weight |
| *myristica fragrans* = | 0.5 % by weight |
| *ocimum gratissimum* = | 0.5 % by weight |
| *origanum heracleoticum* = | 5.0 % by weight |
| *origanum majorana* = | 5.0 % by weight |
| *urtica dioica* = | 5.0 % by weight |

-continued

| | |
|---|---|
| *pimpinella anisum* = | 0.5 % by weight |
| *pinus pinaster* = | 2.0 % by weight |
| *rosmarinus officinalis* = | 10.0 % by weight |
| *salvia officinalis* = | 1.0 % by weight |
| *satureja montana* = | 1.0 % by weight |
| *sesamum indicum* = | 5.0 % by weight |
| *thymus vulgaris* = | 5.0 % by weight |
| *vanilla planifolia* Andrews = | 1.2 % by weight |
| *zingiber officinalis* = | 2.0 % by weight |
| sodium chloride = | 1.0 % by weight. | wherein each active component is derived from at least one of the ingredients, the ingredients providing the following amounts of the active components: eugenol: at least 12% by weight, eugenol acetate: at least 3% by weight, vanillin: at least 0.1% by weight, and carvacrol: at least 0.5% by weight.

2. The Decontaminating composition according to claim 1, wherein the sodium chloride is derived from grey salt.

3. A biodecontaminant material comprising the decontaminating composition according to claim 1, and a carrier for the decontaminating composition, wherein the decontaminating composition is integrated into the carrier.

4. The Biodecontaminant material according to claim 3, wherein the carrier is selected from the group consisting of plastic materials, papers and non-wovens.

5. The Decontaminating composition according to claim 1, further comprising thymol as an active component, the thymol deriving from at least one of the ingredients.

6. The Decontaminating composition according to claim 5, wherein the composition comprises at least 0.5% by weight of thymol.

* * * * *